(12) United States Patent
Sakai et al.

(10) Patent No.: US 9,518,908 B2
(45) Date of Patent: Dec. 13, 2016

(54) FLUID MECHANICAL PROPERTY MEASUREMENT METHOD AND MEASUREMENT DEVICE

(71) Applicant: THE FOUNDATION FOR THE PROMOTION OF INDUSTRIAL SCIENCE, Tokyo (JP)

(72) Inventors: Keiji Sakai, Tokyo (JP); Tomoki Ishiwata, Tokyo (JP)

(73) Assignee: THE FOUNDATION FOR THE PROMOTION OF INDUSTRIAL SCIENCE, Tokyo (JP)

( * ) Notice: Subject to any disclaimer, the term of this patent is extended or adjusted under 35 U.S.C. 154(b) by 229 days.

(21) Appl. No.: 14/391,035

(22) PCT Filed: Mar. 5, 2013

(86) PCT No.: PCT/JP2013/055952
§ 371 (c)(1),
(2) Date: Oct. 7, 2014

(87) PCT Pub. No.: WO2013/161391
PCT Pub. Date: Oct. 31, 2013

(65) Prior Publication Data
US 2015/0068290 A1    Mar. 12, 2015

(30) Foreign Application Priority Data
Apr. 25, 2012    (JP) .................... 2012-099450

(51) Int. Cl.
*G01N 13/02* (2006.01)
*G01N 11/00* (2006.01)
*G01N 11/16* (2006.01)

(52) U.S. Cl.
CPC ............. *G01N 13/02* (2013.01); *G01N 11/00* (2013.01); *G01N 11/16* (2013.01); *G01N 2011/008* (2013.01); *G01N 2013/0241* (2013.01); *G01N 2013/0258* (2013.01)

(58) Field of Classification Search
CPC ..................... G01N 2013/0258; G01N 13/02
USPC .............................................. 73/54.01, 64.48
See application file for complete search history.

(56) References Cited

FOREIGN PATENT DOCUMENTS

| | | |
|---|---|---|
| JP | 2006-153535 A | 6/2006 |
| JP | 2010-271234 A | 12/2010 |
| JP | 2011-252072 A | 12/2011 |

*Primary Examiner* — Michael A Lyons
*Assistant Examiner* — Jean Morello
(74) *Attorney, Agent, or Firm* — Bacon & Thomas, PLLC

(57) ABSTRACT

An object is to measure a mechanical property of a fluid at a temporal resolution of at least 100 [μs]. Therefore, a method comprising: causing a droplet 21 to fly by ejecting a fluid to be measured from a nozzle 11a as the droplet 21; generating an electric field in a space around a flight path 22 of the droplet 21 by applying a voltage to an electrode arranged in the vicinity of the flight path 22; deforming the droplet 21 in a way of contactless deformation with a dielectric force induced by the electric field; and measuring a mechanical property of the fluid based on temporal variation of deformation state of the droplet 21 after deforming the droplet 21.

10 Claims, 8 Drawing Sheets

FLUID MECHANICAL PROPERTY MEASUREMENT METHOD AND MEASUREMENT DEVICE

TECHNICAL FIELD

The present invention relates to a fluid mechanical property measurement method and a measurement device used for the method.

BACKGROUND ART

Conventionally, it has been known that surface tension of fluid may vary every moment after a new surface is generated.

A typical example is a surface-active agent solution. It is a well-known phenomenon that, after its new surface is generated, molecules of the surface-active agent diffuse inside the fluid, reach the surface and adhere to the surface, thereby the surface energy, i.e., the surface tension of the solution gradually reduces. The surface-active agent solution is industrially a very important material. For example, surface-active agents are often blended with inks used for inkjet type printers, so that ink drops may immediately wet and permeate paper immediately after the ink drops being ejected and attached the paper.

Thus, for example, it is very important, in the inkjet technology, to know temporal variation of the surface tension of ink droplets which varies after ejection in order to design nozzles for ejecting ink or to know wettability of ink after attaching to paper.

In cases of the surface-active agents often used industrially, typical time necessary for the surface tension variation by the above-mentioned adhesion ranges between units of is (microsecond) and units of s (second), in their solutions of practical concentration. Specifically, in the solutions of sufficiently practical concentration, it ranges between 10 [μs] and 100 [ms].

On the other hand, there are some methods or devices which measure the time-varying surface tension (For example, refer to Patent Document 1.). Specifically, some methods, such as an oscillation jet method, a maximum bubble pressure method, and a surface tension wave measurement method, have been known.

PRIOR ART DOCUMENT

Patent Document

Patent Document 1: Japanese Patent Application Laid-Open (kokai) No. 2011-252072 (JP 2011-252072 A)

DISCLOSURE OF THE INVENTION

Problems to be Solved by the Invention

However, in the aforementioned conventional methods, it is impossible to measure the surface tension within 1 [ms] after generation of the fluid surface, and it is difficult to measure it precisely within 10 [ms] after the generation. For example, in the oscillation jet method and the maximum bubble pressure method, the temporal resolution is about 1 [ms] at most fineness because of the influence of the viscosity and inertia of fluid. Further, the practical range of the temporal resolution, where the measurement of sufficient accuracy is available, is about 10 [ms].

In the surface tension wave measurement method, although the temporal resolution reaches to several [μs], the measured objects should be the fluid surface with the modulus of surface elasticity below 100 [mN/m], so selection of the measurable objects is extremely restricted. Furthermore, it is indispensable to use a laser apparatus of sufficient coherency and output of more than several [W] or the like, so the devices would be expensive and large-sized.

Besides the surface tension explained above, viscosity is another important physical property of fluid, though there has been hitherto no method to measure the temporal variation of the viscosity of the fluid which constitutes the droplet generated by the inkjet etc.

An object of the present invention is to solve the above-mentioned problems in the conventional technologies and to provide a fluid mechanical property measurement method and a measurement device used for the method, in which a fluid mechanical property(s) can be measured at a temporal resolution of 100 [μs] or higher.

Means for Solving Problems

Accordingly, the present invention provides a fluid mechanical property measurement method, the method comprising: causing a droplet to fly by ejecting a fluid to be measured from a nozzle as the droplet; generating an electric field in a space around a flight path of the droplet by applying a voltage to an electrode arranged in the vicinity of the flight path; deforming the droplet in a way of contactless deformation with a dielectric force induced by the electric field; and measuring a mechanical property of the fluid based on temporal variation of deformation state of the droplet after deforming the droplet.

In another fluid mechanical property measurement method, the mechanical property of the fluid is measured with varying duration, the duration from ejection of the fluid as the droplet to action of the dielectric force induced by the electric field on the droplet.

In yet another fluid mechanical property measurement method, the mechanical property of the fluid is surface tension and/or viscosity.

In yet another fluid mechanical property measurement method, the temporal variation of the deformation state is oscillation of deformation of the droplet, the oscillation is generated by the surface tension acting as restoring force.

In yet another fluid mechanical property measurement method, the oscillation of deformation of the droplet is a damping oscillation damped by the viscosity of the fluid.

In yet another fluid mechanical property measurement method, the following relation $\sigma\rho R/\eta^2 > 1$ is satisfied, when radius of the droplet is represented by R and the surface tension, viscosity, and density of the fluid are represented by $\sigma$, $\eta$, and $\rho$.

The present invention also provides a fluid mechanical property measurement device, the device comprising: a droplet creation device causing a droplet to fly by ejecting a fluid to be measured from a nozzle as the droplet; an electrode disposed in the vicinity of flight path of the droplet; a voltage application device applying a voltage to the electrode; and a droplet observation device observing the droplet, wherein: the voltage application device applies the voltage to the electrode so as to generate an electric field in a space around the flight path, a dielectric force induced by the electric field acts on the droplet in a way of contactless deforming the droplet; and a mechanical property of the fluid is measured based on temporal variation of deformation state of the droplets observed by the droplet observation device after deforming the droplet.

In another fluid mechanical property measurement device, the mechanical property of the fluid is measured with varying duration, the duration from ejection of the fluid as the droplet to action of the dielectric force induced by the electric field on the droplet.

In yet another fluid mechanical property measurement device, the electrode is a pair of needle-like or rod-like members disposed in positions symmetrical about the flight path.

In yet another fluid mechanical property measurement device, the electrode is a pair of parallel members disposed in positions symmetrical about the flight path and extending along the flight path.

Effects of the Invention

According to the present invention, a fluid mechanical property(s) can be measured at a high temporal resolution.

BEST MODES FOR CARRYING OUT THE INVENTION

Embodiments of the present invention will now be described in detail with reference to the drawings.

Figure 1:
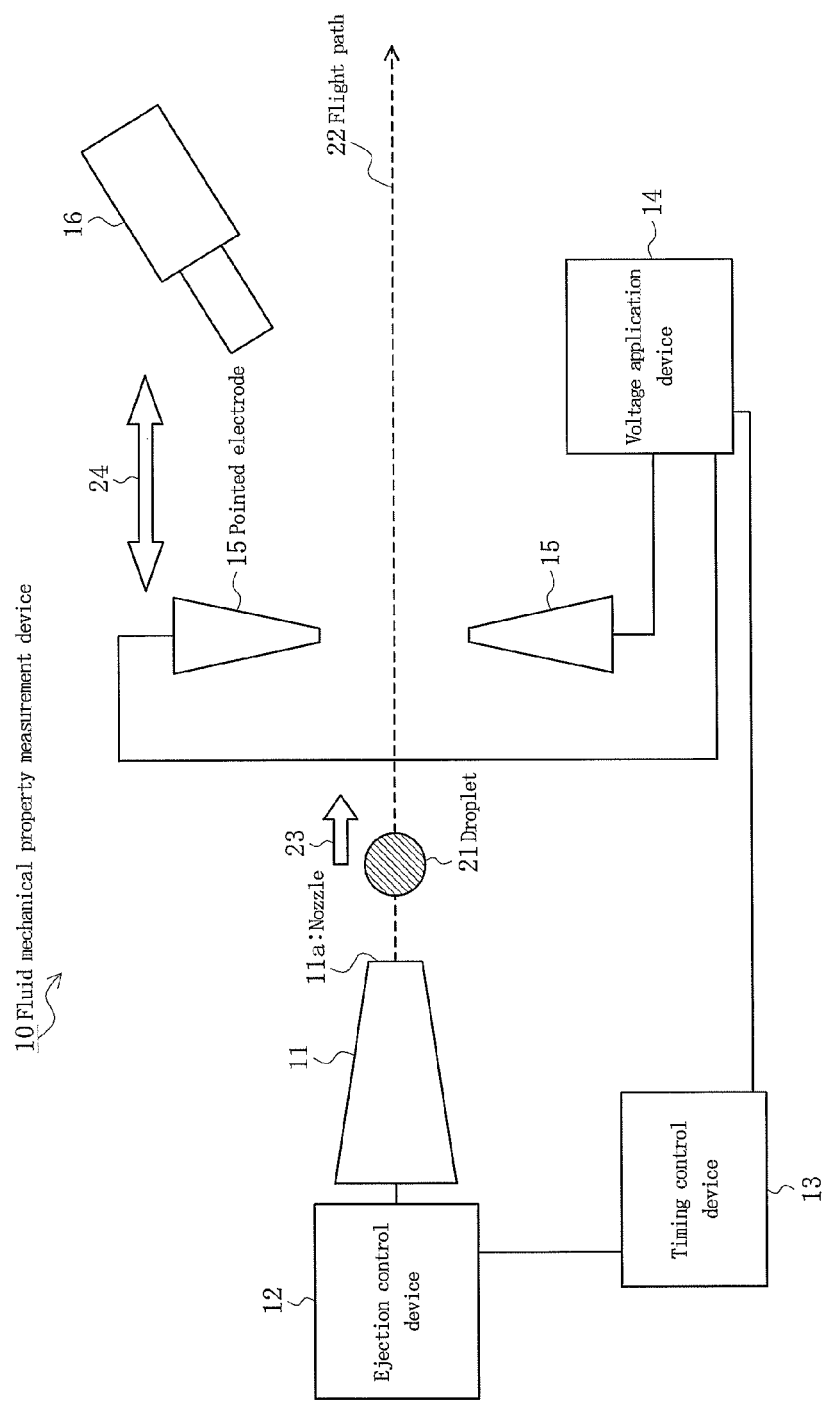
FIG. 1 is a view showing a configuration of a fluid mechanical property measurement device in a first embodiment of the present invention.

FIG. 1 is a view showing a configuration of a fluid mechanical property measurement device in a first embodiment of the present invention.

In the figure, the reference numeral 10 designates a fluid mechanical property measurement device in the present embodiment. The fluid mechanical property measurement device 10 is a device to measure a mechanical property(s) of a fluid which constitutes a droplet 21 after being ejected by targeting the droplet 21 for measuring which is ejected with an initial velocity in an atmosphere or a vacuum. More specifically, it is a device to deform the droplet 21 in a way of contactless deformation from a spherical form, and to measure the mechanical property(s) of the fluid constituting the droplet 21 based on temporal variation of deformation state of the droplet 21 after deformation. In the example shown in the figure, the fluid mechanical property measurement device 10 also includes a droplet creation device which creates the droplet 21 and causes it to fly, and a droplet observation device which observes the temporal variation of deformation state of the droplet 21 after deformation.

The reference numeral 11 designates a head part, which serves as a droplet creation unit and as a portion of the droplet creation device. The head part 11 is provided with an accommodation space which accommodates the fluid inside, and ejects the droplet 21 which is a minute drop of the fluid in the atmosphere or vacuum serving as its outside space. The head part 11 is provided with a nozzle 11a which serves as a minute aperture formed at the tip (the right end in the figure), and the inside of the accommodation space communicates with the outside space through the nozzle 11a.

Notably, the head part 11 uses a so-called inkjet technology of an on-demand type inkjet method, and ejects the droplet 21 by an instantaneous pressure rise at arbitrary time. For example, it works along the same principle as devices creating ink droplets used in inkjet type printers or like, and causes a piezoelectric element, such as a piezo-element arranged in a wall of the accommodation space, to work so as to deform the wall, to pressurize the fluid in the accommodation space, and to eject the droplet 21 from the nozzle 11a by the pressure (For example, refer to Non-Patent Document 1.).

Non-Patent Document 1: A series "digital printer art" inkjet, the first edition, edited by The Imaging Society of Japan, Tokyo Denki University Press, Sep. 10, 2008 issue, the 2-9th page.

The fluid may be composed of any material; for example, a material which have electric conductivity or a material which does not have electric conductivity. Typically, the fluid is a solution of a surface-active agent. However, the fluid may be water, oil, etc., may be ink used for a common inkjet printer, may be gel-like ink, or may be a solution, an organic solvent, silicone oil, etc.

The reference numeral 12 designates an ejection control device for controlling the operation of the head part 11 and letting the head part 11 eject the droplets 21 from the nozzle 11a. The ejection control device 12 is provided with an excitation voltage circuit, which generates a pulse-like voltage signal or the like as a drive signal, and applies the drive signal to the piezoelectric elements provided to the head part 11 so as to let the piezoelectric element work. Thereby, the droplet 21 ejected from the nozzle 11a flies in the direction shown by an arrow 23 along a flight path 22 shown by a straight dotted line. The flight speed of the droplet 21 is about 1-10 [m/s], for example.

The reference numeral 15 designates pointed electrodes, which serve as electrodes to generate an electric field for deforming the droplet 21 from the spherical forms. The pointed electrodes 15 are disposed in the vicinity of the flight path 22 of the droplet 21, and generate the electric field in a space around the flight path 22 of the droplet 21 when a voltage is applied to the pointed electrodes 15. A dielectric force induced by the electric field acts on the droplet 21 in a way of contactless deforming the droplet 21 from the spherical forms. In the example shown in the figure, a pair of pointed electrodes 15 is arranged in the both sides of the flight path 22. Each of the pointed electrodes 15 is a minute member having a rod-like or needle-like shape with a pointed tip, or a long and slender plate-like (knife edge-like) tapered shape with a pointed tip. The pointed tips are positioned in the vicinity of the straight line-like flight path 22, and are arranged to be opposed each other on both sides of the flight path 22 and to be at the same distance from the flight path 22. Also the pointed electrodes 15 are disposed movable in the direction shown by an arrow 24. Thereby, it is possible to adjust the distance from the nozzle 11a to a position on the flight path 22 corresponding to the pointed electrodes 15.

Although the head part 11 is arranged so that the nozzle 11a turns sideways and the flight path 22 of the droplet 21 extends horizontally in the example shown in the figure, the posture of the head part 11 and the extending direction of the flight path 22 are not limited to these. For example, the head part 11 may be arranged so that the nozzle 11a turns up or down and the flight path 22 of the droplet 21 extends perpendicularly, or the head part 11 may be arranged so that the nozzle 11a diagonally turns up or down and the flight path 22 of the droplet 21 extends diagonally.

The reference numeral 14 designates a voltage application device for applying a voltage between a pair of pointed electrodes 15. The voltage application device 14 is provided with a voltage circuit generating a positive or negative voltage signal of about hundreds or thousands [V] or the like, and gives the voltage signal to the pointed electrodes 15 so as to apply the voltage between the pointed electrodes 15 with a desired timing. It is necessary to adjust the timing for applying the voltage to the pointed electrode 15 and the timing for generating the droplet 21 in order to deform the shape of the droplet 21 selectively. Therefore, the voltage application device 14 and the ejection control device 12 are connected with each other through a timing control device 13.

The reference numeral 16 designates an object image detecting device, which is a part of the droplet observation device and is specifically a high speed camera, such as a digital high speed camera. Since the object image detecting device 16 is for observing the temporal variation of the deformation state of the droplet 21 after the deformation by the electric field generated by the pointed electrodes 15, the object image detecting device 16 is arranged so that its image detecting range includes the position on the flight path 22 corresponding to the pointed electrodes 15 and the area subsequent to the position. Also, the object image detecting device 16 is preferably connected transmissibly with a non-illustrated data processing device, such as a personal computer, so that the data, such as detected images, are able to be memorized by memory means, such as semiconductor memories or hard disks, of the data processing device.

Next will be described a performance of the fluid mechanical property measurement device 10 having the above-mentioned structure.

Figure 2:
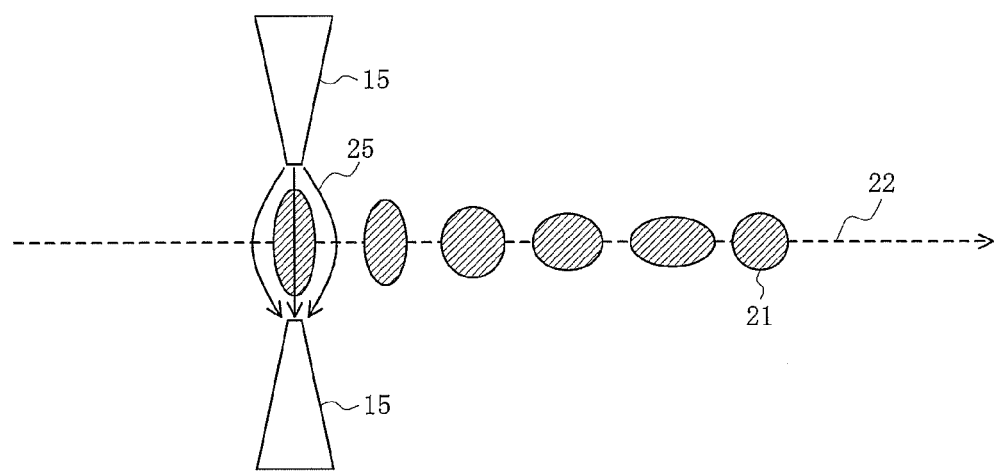
FIG. 2 is a schematic representation showing a state of droplet deformed by an electric field generated by electrodes in the first embodiment of the present invention.

FIG. 2 is a schematic representation showing a state of droplet deformed by an electric field generated by electrodes in the first embodiment of the present invention.

As shown in FIG. 2, in the vicinity of the flight path 22 of the droplet 21, the voltage is applied between a pair of needle-like pointed electrodes 15 disposed symmetrically about the flight path 22, so that the electric field, as shown by an electric force line 25, is generated.

The voltage applied between the pointed electrodes 15 may be a constant voltage, which is applied continuously, or may be a pulse-like voltage, which is applied only for a fixed period when the droplet 21 approaches the pointed electrodes 15.

When being ejected from the nozzle 11a and flying into the vicinity of the pointed electrode 15, the droplet 21 is subject to the dielectric force induced by the electric field generated by the pointed electrodes 15. Assuming that the electric field is uniform, the dielectric force is represented by the following Equation (1), when a permittivity of vacuum is represented by $\varepsilon_0$ and a permittivity of the fluid constituting the droplets 21 is represented by $\varepsilon_r$.

[Expression 1]

$$f(\phi) = \frac{9\varepsilon_0 E_0^2 (\varepsilon_r - \varepsilon_0)^2}{16\pi(\varepsilon_r + 2\varepsilon_0)^2} \left[ \frac{\varepsilon_r + \varepsilon_0}{\varepsilon_r - \varepsilon_0} + \cos(2\phi) \right] \quad \text{Equation (1)}$$

In the Equation (1), $\phi$ represents an angle of elevation based on the direction of the electric field.

Because of this dielectric force, the droplet 21 is subject to tensional stress towards the pair of pointed electrodes 15, so that the droplet 21 deforms into a shape of spheroid with its major axis directing to the pointed electrodes 15.

When flying away from the vicinity of the pointed electrode 15, the droplet 21 becomes not subject to the dielectric force, so that the droplet 21, with its surface tension as restoring force, deforms back into a shape of sphere where its surface energy minimizes. The droplet 21 shows a damping oscillation represented by the following Equation (2), because of its own inertia with its mass and the viscosity of the fluid constituting the droplet 21.

[Expression 2]

$$R(t) = R_0 \exp(i\omega t - \Gamma t) \quad \text{Equation (2)}$$

In the Equation (2), R(t) represents a radius toward rotational symmetry axis of the droplet 21 as a spheroid, $\omega$ represents an angular frequency of the oscillation, and $\Gamma$ represents an attenuation constant of the damping oscillation.

The angular frequency $\omega$ and the attenuation constant $\Gamma$ are represented by the following Equations (3) and (4) respectively, when the surface tension, viscosity, and density of the fluid constituting the droplet 21 are represented by $\sigma$, $\eta$, and $\rho$ respectively.

[Expression 3]

$$\omega = \sqrt{\frac{8\sigma}{\rho R^3}} \quad \text{Equation (3)}$$

$$\Gamma = \frac{5\eta}{\rho R^2} \quad \text{Equation (4)}$$

The object image detecting device 16 takes and records images of the droplet 21 flying with oscillating, and forwards the data of the images to the data processing device. The data processing device computes the angular frequency $\omega$ and the attenuation constant $\Gamma$ of the oscillation of the droplet 21 by processing the data received from the object image detecting device 16.

In the present embodiment, the object image detecting device 16 used for observing the oscillation of the droplet 21 may be the above-mentioned high speed camera, may be a device using a stroboscope observe method for detecting just like a movement of one droplet 21 oscillating continuously by observing plural droplets 21 with a stroboscopic photographical observation, or may be a device using the laser scattering method for observing the oscillation of the droplet 21 based on the varying scattering pattern of laser beam irradiating the oscillating droplet 21.

The surface tension $\sigma$ and the viscosity $\eta$, which are the mechanical properties of the fluid, can be determined through the Equations (3) and (4) from the angular frequency $\omega$ and the attenuation constant $\Gamma$ F of the oscillation of the droplet 21 obtained like this.

By the way, as explained above, for the fluid mechanical property measurement method in the present embodiment, it is necessary that a deformation movement of the droplet 21 should be a damping oscillation remaining for at least one cycle of oscillation or more.

A condition for being such a damping oscillation is to include at least one cycle of oscillation $2\pi/\omega$ or more during damping period $2\pi/\Gamma$, i.e., to be $\omega > \Gamma$.

Then, substituting the Equations (3) and (4) for this condition $\omega > \Gamma$, it turns out that the droplet 21 having radius R and satisfying the relation represented by the following Equation (5) can be the object of observation.

$$\sigma \rho R / \eta^2 > 1 \qquad \text{Equation (5)}$$

The Equation (5) is the condition for oscillating at least two or more times, by the time of fading out. Almost all the surface-active agent solutions with practical concentration are considered to satisfy this condition.

Next will be described the measurement time needed for determining the surface tension $\sigma$, i.e., the temporal resolution of the fluid mechanical property measurement method in the present embodiment.

In the present embodiment, as for the measuring time of the oscillation needed for determining angular frequency, it is not necessary to observe continuously until the induced oscillation of the droplet 21 fades out. For example, it is enough for the measurement time to be time T since the length of in the direction of rotation symmetry axis of the droplet 21 takes the maximum value until it takes the maximum value again, or, further, to be time T/2 since it takes the maximum value until it takes the minimum value.

The angular frequency A of the oscillation is represented by $\omega = 2\pi/T$ from the time T.

Thereby, when the measurement time is represented by time T, for example, the time required to measure the value of the surface tension is represented by the following Equation (6), and this becomes the temporal resolution of the surface tension measurement.

[Expression 4]

$$T = 2\pi \sqrt{\frac{\rho R^3}{8\sigma}} \qquad \text{Equation (6)}$$

For example, when supposing $\sigma=0.05$ [N/m], the density is 1000 [kg/m$^3$], and the radius of the droplet 21 is R=10 [μm] as typical examples of properties of surface-active agent solutions, it is apparent that T=10 [μs] from the Equation (6). Therefore, it is said that the fluid mechanical property measurement method in the present embodiment has a higher temporal resolution than the conventional surface tension measurement method.

The surface of the droplet 21 is generated at the time when the droplet 21 is ejected. Until the above mentioned oscillation begins, the duration of the flight of the droplet 21 from the nozzle 11a to the place of oscillation has passed since the droplet 21 was generated.

Therefore, the surface tension and the viscosity, which are observed and measured by the fluid mechanical property measurement method in the present embodiment, are respectively the surface tension of the fluid surface, which has passed through the duration of the flight from its generation to the place of oscillation, and the viscosity of the fluid just under the surface.

Consequently, it is made out the duration from generation to oscillation of the fluid surface can be arbitrarily varied by moving the position of the pointed electrodes 15 along the direction of the flight path 22, as shown by the arrow 24 in FIG. 1. Thus, it is possible to measure the variation of the surface tension of the fluid surface after its generation by measuring the surface tension and the viscosity of the fluid with varying the position of the pointed electrodes 15.

Next will be described the result of experiments the present inventors performed.

Figure 3:
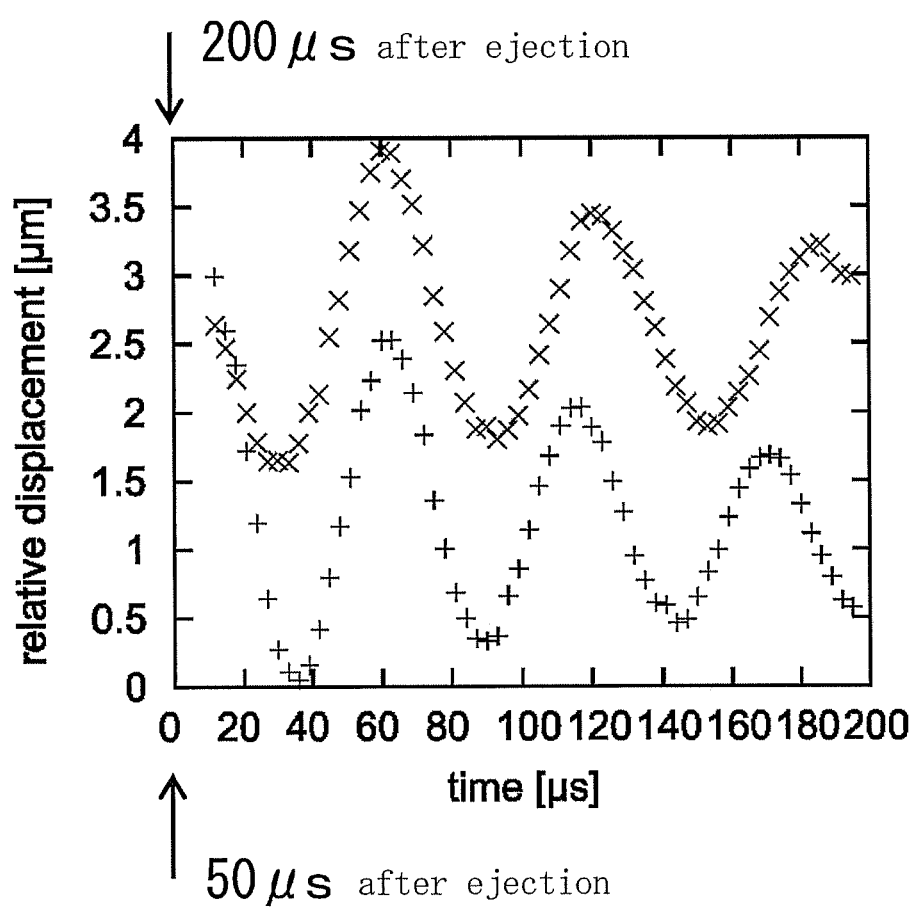
FIG. 3 is a graph showing a temporal variation of an oscillation state of the droplet in the first embodiment of the present invention.
Figure 4:
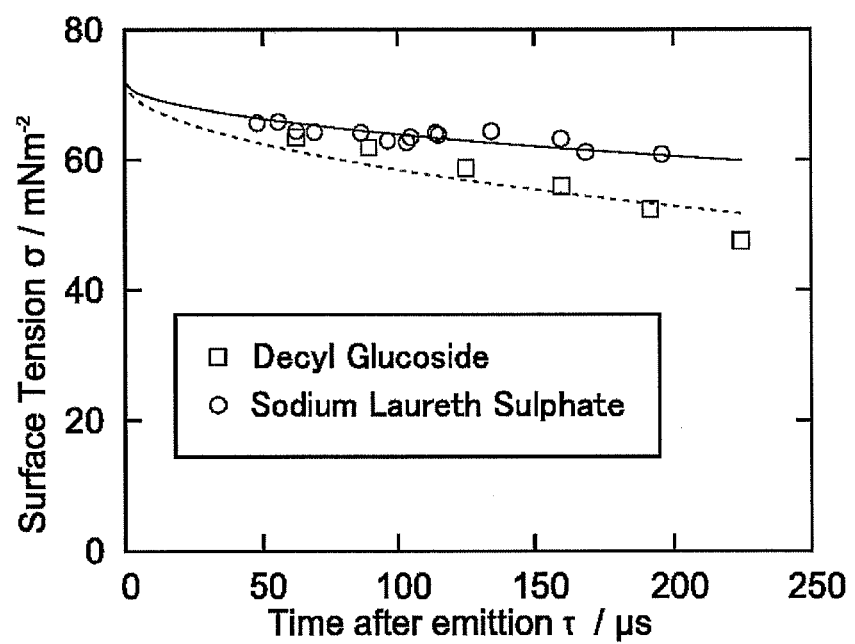
FIG. 4 is a graph showing a temporal variation of a surface tension of the droplet in the first embodiment of the present invention.

FIG. 3 is a graph showing a temporal variation of an oscillation state of the droplet in the first embodiment of the present invention. FIG. 4 is a graph showing a temporal variation of a surface tension of the droplet in the first embodiment of the present invention.

The present inventors produced the head part 11 of the fluid mechanical property measurement device 10 by a glass capillary tube whose tip part was narrowed, provided a piezoelectric element on the outface of the side wall of the head part 11, and gave pressure to the fluid accommodated inside the head part 11 by operating the piezoelectric element, so that the droplet 21 was ejected from the nozzle 11a by the pressure and the experiments were performed.

In these experiments, the surface-active agent solution (1 [wt %] solution of Decyl Glucoside [brand name: Kao Mydol 10] and 1 [wt %] solution of Sodium Laureth Sulphate) was employed as the fluid.

FIG. 3 shows, as graphs, the results of observing the oscillation state of the droplet 21, which was the droplet of the surface-active agent solution (solution of Decyl Glucoside), after the oscillations were induced at different times while the position of the pointed electrode 15 were varying. In FIG. 3, the start time of the oscillation in a lower graph (graph plotted by +) is 50 [μs] after ejection of the droplet 21. And also, in FIG. 3, the start time of the oscillation in an upper graph (graph plotted by x) is 200 [μs] after the ejection of the droplet 21.

FIG. 3 illustrates that, in the later started oscillation, the oscillating cycle is longer and the angular frequency of the oscillation is smaller. Accordingly it illustrates that, in the later started oscillation, the surface tension reduces as time goes by.

FIG. 4 shows, as graphs, the results of measuring the surface tension values of the droplet 21, which was the droplet of the surface-active agent solution (solution of Decyl Glucoside and solution of Sodium Laureth Sulphate), after the oscillations were started at various times. In FIG. 4, the graph plotted by □ shows the case of the droplet 21 of Decyl Glucoside solution, and the graph plotted by ○ shows the case of the droplet 21 of Sodium Laureth Sulphate solution.

FIG. 4 illustrates that the surface tension gradually reduces as time goes by after the generation of the surface.

As described above, according to the fluid mechanical property measurement method in the present embodiment, it is possible to measure the temporal variation of the surface tension with the temporal resolution shorter than 100 [μs].

It is also possible to measure other mechanical properties of the fluid, i.e., those other than the surface tension and the viscosity, according to the fluid mechanical property measurement method in the present embodiment.

For example, when the fluid gels during flight and has an elastic modulus, an oscillation frequency of deformation of the droplet 21 increase since the elastic modulus works as a restoring force to the deformation of the droplet 21. As the variation of the surface tension generally works in the direction to decrease the oscillation frequency with time, when the oscillation frequency increases, it can be supposed to be caused by gelling.

In case that the surface tension is known as invariable with gelling, it is possible to determine the elastic modulus quantitatively from the oscillation frequency variation.

For example, in case that an adsorption molecular film exists on the surface of the droplet 21, the surface viscosity and the surface elasticity appear on the fluid surface. These are a two-dimensional hardness and a two-dimensional stickiness the fluid surface possesses.

Since these physical quantities slightly vary the oscillation frequency and the attenuation constant of the droplet 21, it is possible, for example, to presume the variations of the surface viscosity or the surface elasticity from the variations of the oscillation frequency and the attenuation constant of the droplet 21 in case that the fluid of known viscosity is the objective of measurement.

Next, a second embodiment of the present invention will be described. Structural features similar to the first embodiment are denoted by common reference materials, and repeated description of operation and effects similar to those of the first embodiment is omitted.

Figure 5:
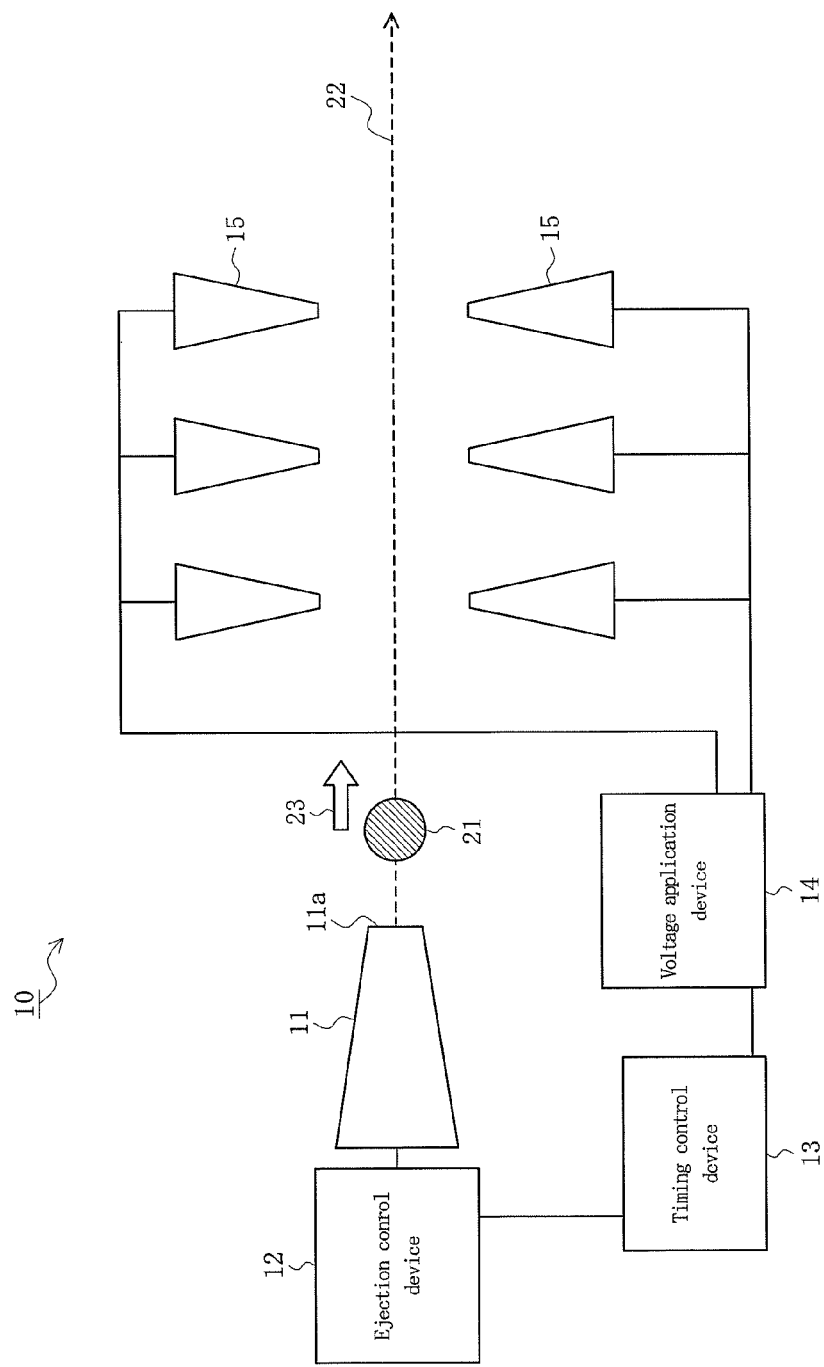
FIG. 5 is a view showing a configuration of a fluid mechanical property measurement device in a second embodiment of the present invention.

FIG. 5 is a view showing a configuration of a fluid mechanical property measurement device in a second embodiment of the present invention.

As shown in FIG. 5, the fluid mechanical property measurement device 10 in the present embodiment has plural pairs (3 pairs in the example shown in the figure) of pointed electrodes 15. And the pairs of pointed electrodes 15 are respectively arranged to be in a row along the flight path 22 of the droplets 21. Thereby, it is possible to measure the temporal variation of the mechanical properties of the fluid, without moving the position of the pointed electrodes 15 along the direction of the flight path 22 as described in the first embodiment.

In FIG. 5, the depiction of the object image detecting device 16 is omitted. Other points in structures and operations are similar to those explained in the first embodiment, therefore description about them is omitted.

Next, a third embodiment of the present invention will be described. Structural features similar to the first and second embodiments are denoted by common reference materials, and repeated description of operation and effects similar to those of the first and second embodiments is omitted.

Figure 6:
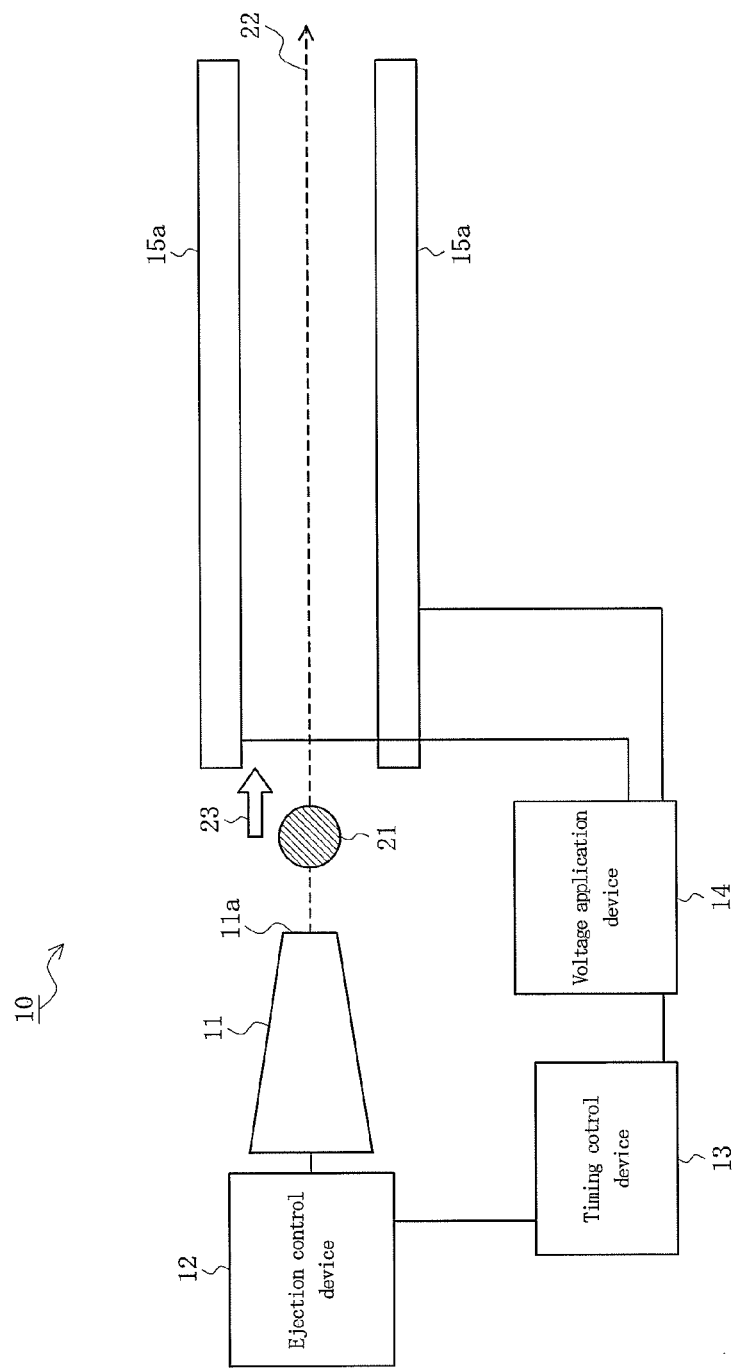
FIG. 6 is a view showing a configuration of a fluid mechanical property measurement device in a third embodiment of the present invention.

FIG. 6 is a view showing a configuration of a fluid mechanical property measurement device in a third embodiment of the present invention.

As shown in FIG. 6, the fluid mechanical properties measurement device 10 in the present embodiment has a pair of parallel electrodes 15*a* which serves as electrodes to generate an electric field for deforming the droplets 21 from the spherical forms. Each parallel electrode 15*a*, for example, is made of a plate-like member, and is positioned in the vicinity of the flight path 22 in a way that the plane of the electrode 15*a* extends in both the direction along the flight path 22 (the left-right direction in the plan) and the direction perpendicular to the flight path 22 (the direction perpendicular to the plan). And also the parallel electrodes 15*a* are arranged to be opposed each other on both sides of the flight path 22, to be parallel each other, and to be at the same distance from the flight path 22. That is, the parallel electrodes 15*a* are arranged along the flight path 22 in a range of predetermined length.

And the deformation of the droplet 21 is achieved by applying a pulse-like voltage to the parallel electrodes 15*a* at an arbitrary time after ejection of the droplet 21 from the nozzle 11*a* of the head part 11.

Therefore, in the present embodiment, it is possible to vary the time to induce the deformation of the droplet 21 just through controlling the shape and timing of the voltage to be applied by the timing control device 13. Thereby, it is possible to measure the temporal variation of the mechanical property of the fluid.

Notably, the parallel electrodes 15*a* are not necessarily made of plate-like members if they extend along the flight path 22 in a range of predetermined length. For example, they may be made of members which are long in the direction along the flight path 22 (the left-right direction in the plan) but are narrow in the direction perpendicular to the flight path 22 (the direction perpendicular to the plan), i.e., plate-like or rod-like members with thin thickness.

It is also possible to replace either of a pair of parallel electrodes 15*a* with a pointed electrode 15.

In FIG. 6, the depiction of the object image detecting device 16 is omitted. Other points in structures and operations are similar to those explained in the first and second embodiments, therefore description about them is omitted.

Next, a fourth embodiment of the present invention will be described. Structural features similar to the first through third embodiments are denoted by common reference materials, and repeated description of operation and effects similar to those of the first through third embodiments is omitted.

Figure 7:
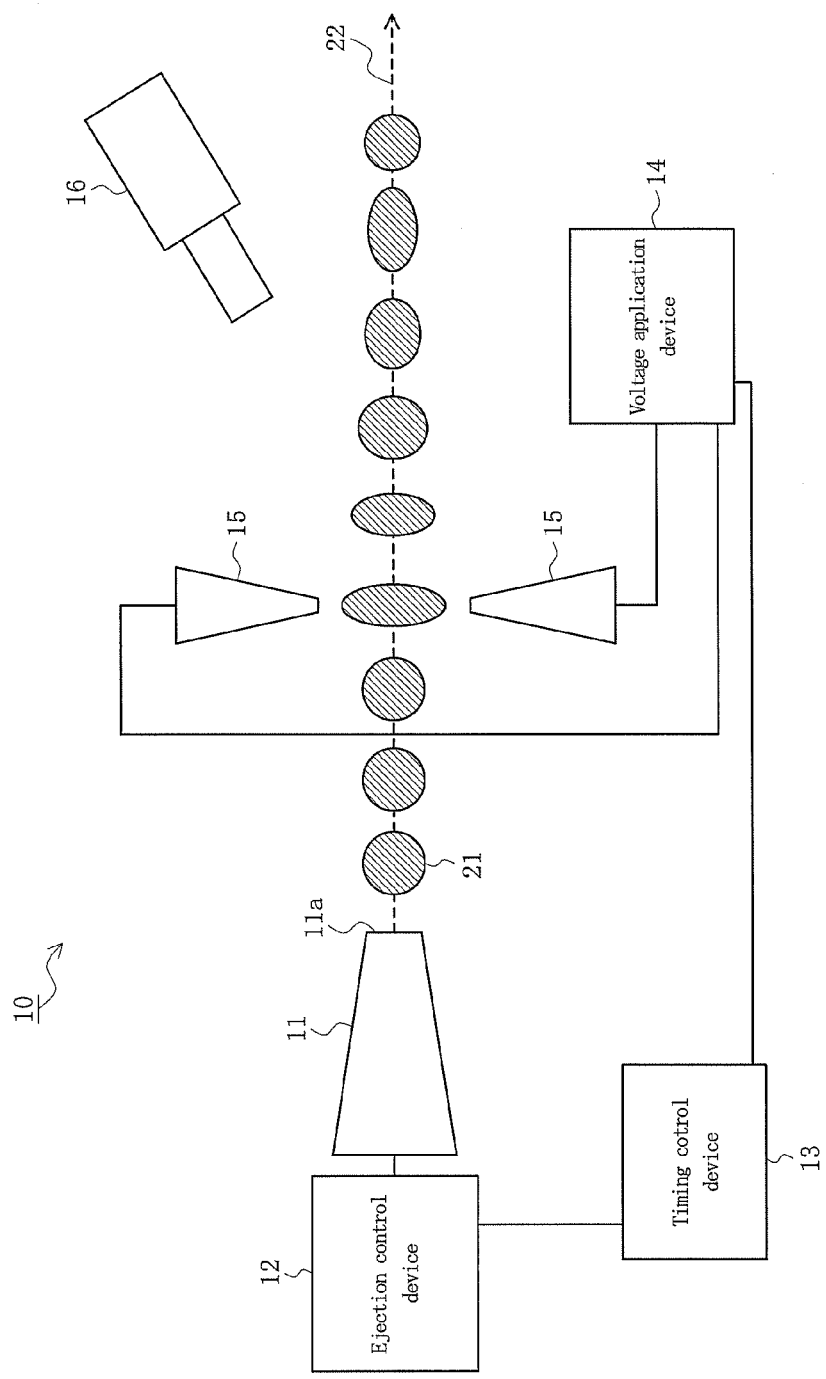
FIG. 7 is a view showing a configuration of a fluid mechanical property measurement device in a fourth embodiment of the present invention.

FIG. 7 is a view showing a configuration of a fluid mechanical property measurement device in a fourth embodiment of the present invention.

As shown in FIG. 7, in the present embodiment, the droplets 21 are continuously ejected from the nozzle 11*a* of the head part 11. In this case, the head part 11 utilizes a technology, so-called an inkjet technology of continuous inkjet type, to generate minute droplets by breaking up a continuously ejected fluid column. For example, the head part 11, with using the power of a pump, applies vibration to the fluid column ejected from the nozzle 11*a*, so that the fluid column is broken up and the droplets 21 are continuously generated. (For example, refer to Non-Patent Document 1.).

The present inventors produced the head part 11 of the fluid mechanical property measurement device 10 by a glass capillary tube whose tip part was narrowed, provided a piezoelectric element on the outface of the side wall of the head part 11, and let the piezoelectric element vibrate. Thereby, pressure waves were applied to the head part 11 from outside, were transmitted along the wall of the head part 11, and were superposed on the constant pressure applied by a non-illustrated pump, so that a fluid column of periodically varying diameter was ejected from the nozzle 11*a* of the head part 11. The fluid column was broken up as the periodic diameter variation grew up, so that the droplets 21 were continuously generated.

In the present embodiment, a constant voltage is continuously applied to a pair of pointed electrodes 15, and a deformation of the droplet 21 is induced at the time the droplet 21 flies through the vicinity of the pointed electrodes 15. For this reason, at a certain moment, as shown in FIG. 7, the shape variation of the droplets 21 can be continuously traced along the flight path 22 from just under the pointed electrodes 15, so that the oscillation state of the droplet 21 after passing the pointed electrodes 15 can be grasped.

Therefore, in the present embodiment, it is possible to obtain a still image including continuously varying shapes of the droplets 21 along the flight path 22 from just under the pointed electrodes 15 as shown in FIG. 7, if a non-illustrated stroboscopic device is arranged, and if a still picture is taken by the object image detecting device 16 with the stroboscopic device glowing at a certain moment, such as a moment one of the droplets 21 passes across between the pointed electrodes 15. Thereby, it is possible to measure the mechanical property of the fluid by observing the oscillation state of the droplet 21 in the still picture.

The present embodiment has been described as an example with the head part 11 utilizing an inkjet technology of continuous inkjet type, though the head part 11 may utilize an inkjet technology of an on-demand type inkjet method, the same as in the first embodiment, so far as it can continuously eject the droplets 21. Other points in structures and operations are similar to those explained in the first through third embodiments, therefore description about them is omitted.

As described above, according to the present embodiment, the mechanical property of the fluid can be measured by observing the oscillation state of the droplet 21, without an expensive high speed camera or a large-scale rapid sequence camera device using stroboscopic method.

Next, a fifth embodiment of the present invention will be described. Structural features similar to the first through fourth embodiments are denoted by common reference materials, and repeated description of operation and effects similar to those of the first through fourth embodiments is omitted.

Figure 8:
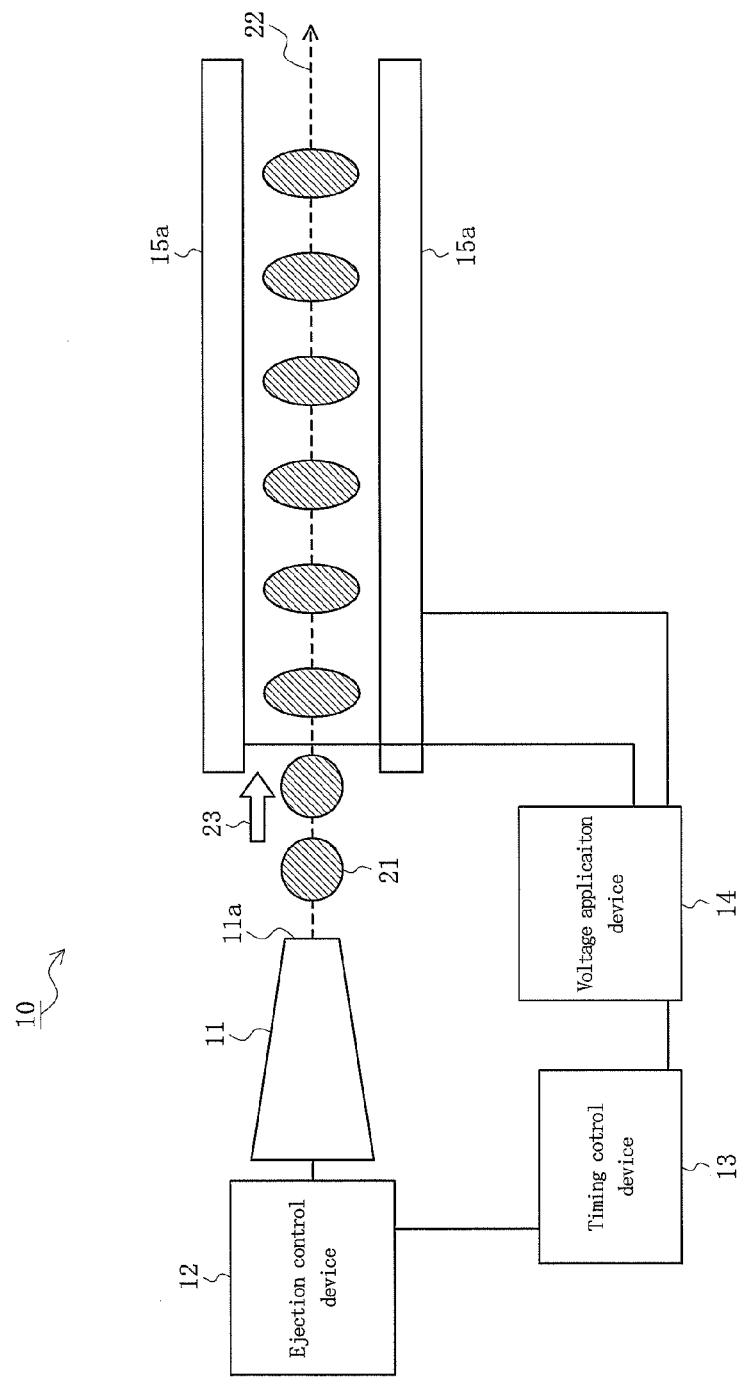
FIG. 8 is a view showing a configuration of a fluid mechanical property measurement device in a fifth embodiment of the present invention.

FIG. 8 is a view showing a configuration of a fluid mechanical property measurement device in a fifth embodiment of the present invention.

As shown in FIG. 8, the fluid mechanical property measurement device 10 in the present embodiment, the same as in the third embodiment, has a pair of parallel electrodes 15a which serves as electrodes to generate an electric field for deforming the droplets 21 from the spherical forms. The droplets 21 are continuously ejected from the nozzle 11a of the head part 11, the same as in the fourth embodiment.

In the present embodiment, a pulse-like voltage is applied to the pair of parallel electrodes 15a. Therefore, the voltage is applied at the same time to all the droplets 21 that exist in a range of predetermined length along the flight path 22 corresponding to the parallel electrodes 15a. Thereby, deformation is simultaneously induced to all the droplets 21. From another viewpoint, deformation is induced to each droplet 21 at the timing after the different duration from each generation.

For this reason, the surface tension after generation of the fluid surface or the time dependence of the viscosity can be observed and measured at once by observing and measuring the temporal variation of the oscillation state of the droplet 21 after induction of deformation by application of a voltage pulse about all the continuous droplets 21.

In FIG. 8, the depiction of the object image detecting device 16 is omitted. Other points in structures and operations are similar to those explained in the third and fourth embodiments, therefore description about them is omitted.

As described above, according to the present embodiment, the temporal variation of the oscillation state of a plurality of droplets 21, which exist in a range of predetermined length along the flight path 22, can be observed and measured simultaneously, and the surface tension after generation of the fluid surface or the time dependence of the viscosity can be observed and measured at once.

The present invention is not limited to the above-described embodiments, but may be diversely modified and varied. Thus, the modifications and variations are not excluded from the scope of protection oh the present invention.

INDUSTRIAL APPLICABILITY

The present invention is applicable to a fluid mechanical property measurement method and a measurement device used for the method.

DESCRIPTION OF REFERENCE NUMERALS

10: Fluid mechanical property measurement device
11a: Nozzle
14: Voltage application device
15: Pointed electrode
15a: Parallel electrode
21: Droplet
22: Flight path

The invention claimed is:

1. A fluid mechanical property measurement method, the method comprising:
   causing a droplet to fly by ejecting a fluid to be measured from a nozzle as the droplet;
   generating an electric field in a space around a flight path of the droplet by applying a voltage to an electrode arranged in the vicinity of the flight path;
   deforming the droplet in a way of contactless deformation with a dielectric force induced by the electric field; and
   measuring a mechanical property of the fluid based on temporal variation of deformation state of the droplet after deforming the droplet.

2. The fluid mechanical property measurement method according to claim 1, wherein the mechanical property of the fluid is measured with varying duration, the duration from ejection of the fluid as the droplet to action of the dielectric force induced by the electric field on the droplet.

3. The fluid mechanical property measurement method according to claim 1, wherein the mechanical property of the fluid is surface tension and/or viscosity.

4. The fluid mechanical property measurement method according to claim 1, wherein the temporal variation of the deformation state is oscillation of deformation of the droplet, the oscillation is generated by the surface tension acting as restoring force.

5. The fluid mechanical property measurement method according to claim 4, wherein the oscillation of deformation of the droplet is a damping oscillation damped by the viscosity of the fluid.

6. The fluid mechanical property measurement method according to claim 1, wherein the following relation $$\sigma \rho R/\eta^2 > 1$$

is satisfied, when radius of the droplet is represented by R and the surface tension, viscosity, and density of the fluid are represented by $\sigma$, $\eta$, and $\rho$.

7. A fluid mechanical property measurement device, the device comprising: a droplet creation device causing a droplet to fly by ejecting a fluid to be measured from a nozzle as the droplet; an electrode disposed in the vicinity of flight path of the droplet;
   a voltage application device applying a voltage to the electrode; and
   a droplet observation device observing the droplet, wherein:
   the voltage application device applies the voltage to the electrode so as to generate an electric field in a space around the flight path, a dielectric force induced by the electric field acts on the droplet in a way of contactless deforming the droplet; and a mechanical property of the fluid is measured based on temporal variation of deformation state of the droplet observed by the droplet observation device after deforming the droplet.

8. The fluid mechanical property measurement device according to claim 7, wherein the mechanical property of the fluid is measured with varying duration, the duration from ejection of the fluid as the droplet to action of the dielectric force induced by the electric field on the droplet.

9. The fluid mechanical property measurement device according to claim 7, wherein the electrode is a pair of needle-like or rod-like members disposed in positions symmetrical about the flight path.

10. The fluid mechanical property measurement device according to claim 7, wherein the electrode is a pair of parallel members disposed in positions symmetrical about the flight path and extending along the flight path.

* * * * *